United States Patent
Odom et al.

(10) Patent No.: US 10,892,525 B2
(45) Date of Patent: Jan. 12, 2021

(54) RECHARGEABLE BATTERIES INCLUDING HIGH-VOLTAGE CATHODE AND REDOX SHUTTLE CONFERRING OVERCHARGE PROTECTION

(71) Applicant: University of Kentucky Research Foundation, Lexington, KY (US)

(72) Inventors: Susan A. Odom, Lexington, KY (US); Aman Preet Kaur, Lexington, KY (US); Corrine F. Elliott, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/637,971

(22) Filed: Jun. 29, 2017

(65) Prior Publication Data
US 2018/0006336 A1 Jan. 4, 2018

Related U.S. Application Data

(60) Provisional application No. 62/356,388, filed on Jun. 29, 2016.

(51) Int. Cl.
*H01M 10/42* (2006.01)
*H01M 8/18* (2006.01)
(Continued)

(52) U.S. Cl.
CPC ...... *H01M 10/4235* (2013.01); *C07D 241/46* (2013.01); *H01M 4/136* (2013.01);
(Continued)

(58) Field of Classification Search
None
See application file for complete search history.

(56) References Cited

U.S. PATENT DOCUMENTS 8,101,302 B2  1/2012  Lamanna et al.
2008/0244296 A1 * 10/2008 Kangas ............... G06F 1/30
                                          713/330

(Continued)

OTHER PUBLICATIONS

Orlova et al (Chemical Abstract (accession No. 1982:20048; document No. 96:20048)—English abstract for "Some reactions of 10-phenyloctafluorophenothiazine and its oxide", Izvestiya Sibirskogo Otdeleniya Akademii Nauk SSSR, Seriya Khimicheskikh Nauk (1981), (Year: 1981).*

(Continued)

*Primary Examiner* — Amanda C. Walke
(74) *Attorney, Agent, or Firm* — Stites & Harbison PLLC; Mandy Wilson Decker; Summer E. Young

(57) ABSTRACT

Compounds for use as photoredox catalysts and as redox shuttles in a rechargeable battery having a high-voltage cathode providing overcharge protection capabilities are provided, including a compound according to the formula:

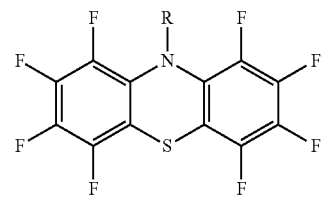

wherein R is selected from the group consisting of alkyl, aryl, alkylaryl, alkoxyaryl, alkylcarboxyl, aryl carbonyl, haloalkyl, perfluoroalkyl, glycols, haloaryl, a negative electrolyte, and a polymer.

20 Claims, 7 Drawing Sheets

EPT

BCF3EPT

BC2F5EPT

DCNEPT

DNO2EPT

OFEPT

(51) Int. Cl.
| | |
|---|---|
| H01M 10/0525 | (2010.01) |
| H01M 4/136 | (2010.01) |
| H01M 4/58 | (2010.01) |
| H01M 10/0567 | (2010.01) |
| C07D 241/46 | (2006.01) |
| H01M 4/587 | (2010.01) |

(52) U.S. Cl.
CPC ........... *H01M 4/5825* (2013.01); *H01M 8/18* (2013.01); *H01M 8/188* (2013.01); *H01M 10/0525* (2013.01); *H01M 10/0567* (2013.01); *H01M 4/587* (2013.01); *H01M 2220/30* (2013.01); *Y02E 60/50* (2013.01)

(56) References Cited

U.S. PATENT DOCUMENTS

| | | | |
|---|---|---|---|
| 2008/0296169 A1* | 12/2008 | Davidson | C25B 1/04 205/337 |
| 2009/0286162 A1 | 11/2009 | Lamanna et al. | |
| 2011/0294017 A1 | 12/2011 | Weng et al. | |
| 2011/0294018 A1 | 12/2011 | Zhang et al. | |
| 2016/0208030 A1* | 7/2016 | Gavvalapalli | C08F 112/14 |
| 2017/0062842 A1* | 3/2017 | Huang | C07D 279/22 |
| 2017/0244132 A1* | 8/2017 | Wagner | H01M 10/0525 |
| 2018/0154086 A1* | 6/2018 | Toporek | A61M 5/31551 |

OTHER PUBLICATIONS

Kaur et al ("Overcharge protection of lithium-ion batteries above 4 V with a perfluorinated phenothiazine derivative", Journal of Materials Chemistry A, vol. 4 (15), p. 5410-5414 (2016)). (Year: 2016).*
Arora, et al., Capacity Fade Mechanisms and Side Reactions in Lithium-Ion Batteries, Electrochem. Soc., 1998, 145, 3647-3667.
Balakrishnan, et al., Safety mechanisms in lithium-ion batteries, Power Sources, 2006, 155, 401-414.
Chen, et al., Chemical Overcharge and Overdischarge Protection for Lithium-Ion Batteries, Electrochem. Solid-State Lett., 2005, 8, A59-A62.
Chen, et al., Redox shuttles for safer lithium-ion batteries, Electrochim. Acta, 2009, 54, 5605-5613.
Buhrmester, et al., Possible Redox Shuttle Additives for Chemical Overcharge and Overdischarge Protection for Lithium-Ion Batteries, J. Electrochem. Soc., 2006, 153, A288-A294.
Buhrmester, et al., Studies of Aromatic Redox Shuttle Additives for LiFePO4-Based Li-Ion Cells, J. Electrochem. Soc., 2005, 152, A2390-A2399.
Dahn, et al., High-Rate Overcharge Protection of LiFePO4-Based Li-Ion Cells Using the Redox Shuttle Additive 2,5-Ditertbutyl-1,4-dimethoxybenzene, J. Electrochem. Soc., 2005, 152, A1283-A1289.
Buhrmester, et al., The Use of 2,2,6,6-Tetramethylpiperinyl-Oxides and Derivatives for Redox Shuttle Additives in Li-Ion Cells, J. Electrochem. Soc., 2006, 153, A1800-A1804.
Moshurchak, et al., Triphenylamines as a Class of Redox Shuttle Molecules for the Overcharge Protection of Lithium-Ion Cells, J. Electrochem. Soc., 2008, 155, A129-A131.
Kaur, et al., 3,7-Bis(trifluoromethyl)-N-ethylphenothiazine: a redox shuttle with extensive overcharge protection in lithium-ion batteries, J. Mater. Chem. A, 2014, 2, 18190-18193.
Kaur, et al., Overcharge Performance of 3,7-Bis(trifluoromethyl)-Nethylphenothiazine at High Concentration in Lithium-Ion Batteries, J. Electrochem. Soc., 2015, 163, A1-A7.
Zang, et al., Molecular engineering towards safer lithium-ion batteries: a highly stable and compatible redox shuttle for overcharge protection, Energy Environ. Sci., 2012, 5, 8204-8207.
Forgie, et al., Electrochemical characterisation of a lithium-ion battery electrolyte based on mixtures of carbonates with a ferrocene-functionalised imidazolium electroactive ionic liquid, Phys. Chem. Chem. Phys., 2013, 15, 7713-7721.

Khakani, et al., Redox Shuttles for Lithium-Ion Batteries at Concentrations up to 1 M Using an Electroactive Ionic Liquid Based on 2,5,di-tert-butyl-1,4-dimethoxybenzene, J. Electrochem. Soc., 2015, 162, A1432-A1438.
Ergun, et al., Overcharge performance of 3,7-disubstituted N-ethylphenothiazine derivatives in lithium-ion batteries, Chem. Commun., 2014, 50, 5339-5341.
Hu, et al., Recent progress in high-voltage lithium ion batteries, J. Power Sources, 2013, 237, 229-242.
Moshurchak, et al., High-Potential Redox Shuttle for Use in Lithium-Ion Batteries, J. Electrochem. Soc., 2009, 156, A309-A312.
Zhang, et al., Novel redox shuttle additive for high-voltage cathode materials, Energy Environ. Sci., 2011, 4, 2858-2862.
Huang, et al., An organophosphine oxide redox shuttle additive that delivers long-term overcharge protection for 4 V lithium-ion batteries, J. Mater. Chem. A, 2015, 3, 10710-10714.
Casselman, et al., The fate of phenothiazine-based redox shuttles in lithium-ion batteries, Phys. Chem. Chem. Phys., 2015, 17, 6905-6912.
Narayana, et al., N-Substituted Phenothiazine Derivatives: How the Stability of the Neutral and Radical Cation Forms Affects Overcharge Performance in Lithium-Ion Batteries, ChemPhysChem, 2015, 16, 1179-1189.
Ergun, et al., Controlling Oxidation Potentials in Redox Shuttle Candidates for Lithium-Ion Batteries, J. Phys. Chem. C, 2014, 118, 14824-14832.
Odom, et al., A fast, inexpensive method for predicting overcharge performance in lithium-ion batteries, Energy Environ. Sci., 2014, 7, 760-767.
Brushett, et al., An All-Organic Non-aqueous Lithium-Ion Redox Flow Battery, Adv. Energy Mater., 2012, 2, 1390-1396.
Huang, et al., Liquid Catholyte Molecules for Nonaqueous Redox Flow Batteries, Adv. Energy Mater., 2015, 5, 1401782-1401788.
Kaur, et al., A Highly Soluble Organic Catholyte for Non-Aqueous Redox Flow Batteries, Energy Tech., 2015, 3, 476-480.
Wei,et al., TEMPO-Based Catholyte for High-Energy Density Nonaqueous Redox Flow Batteries, Adv. Mater., 2014, 26, 7649-7653.
Lacey, et al., A redox shuttle to facilitate oxygen reduction in the lithium air battery, Electrochem. Commun., 2013, 26, 74-76.
Treat, et al., Metal-Free Atom Transfer Radical Polymerization, J. Am. Chem. Soc., 2014, 136, 16096-16101.
Pan, et al., Photoinduced Metal-Free Atom Transfer Radical Polymerization of Acrylonitrile, ACS Macro Letters, 2015, 4, 192-196.
Tomilin, et al., Cation Radicals of N-Substituted Phenothiazines, Chem. Heterocycl. Compd., 1996, 32, 365-370.
Yakobson, et al., Aromatic nucleophilic substitution, Zhurnal Obshchei Khimii 1967, 37, 1289-1293.
Belf, et al., Octafluorophenothiazine, Chem. Industry, 1966, 6, 238-239.
Sheldrick, G., SHELXT—Integrated space-group and crystalstructure determination, Acta Crystallog. Sect. A, 2015, 71, 3-8.
Sheldrick, G., Crystal structure refinement with SHELXL, Acta Crystallog. Sect. C, 2015, 71, 3-8.
Becke, A. D., Density-functional thermochemistry. III. The role of exact exchange, J. Chem. Phys., 1993, 98, 5648-5652.
Lee,et al. Parr, Development of the Colic-Salvetti correlation-energy formula into a functional of the electron density, Physical Review B, vol. 37 (2), 1988, pp. 785-789.
McLean, et al., Contracted Gaussian basis sets for molecular calculations. I. Second row atoms, Z=11-18, J. Chem. Phys., 1980, 72, 5639-5648.
Krishnan, et al , Self-consistent molecular orbital methods. XX. A basis set for correlated wave functions, J. Chem. Phys., 1980, 72, 650-654.
Chen, et al., Bifunctional electrolyte additive for lithium-ion batteries, Electrochem. Commun., 2007, 9, 703-707.
Kaur, et al., Overcharge protection of lithium-ion batteries above 4 V with a perfluorinated phenothiazine derivative J. of Materials Chemistry A, 2016, 4, 5410-5414.

\* cited by examiner

RECHARGEABLE BATTERIES INCLUDING HIGH-VOLTAGE CATHODE AND REDOX SHUTTLE CONFERRING OVERCHARGE PROTECTION

PRIORITY

This invention claims priority to U.S. Provisional Application Ser. No. 62/356,388 filed Jun. 29, 2016.

GOVERNMENT INTEREST

This invention was made with government support under grant number CHE-1300653 awarded by the National Science Foundation. The government has certain rights in the invention.

TECHNICAL FIELD

The presently-disclosed subject matter generally relates to rechargeable batteries and compounds for use in conferring overcharge protection in such batteries. In particular, certain embodiments of the presently-disclosed subject matter relate to batteries having a high-voltage cathode, and compounds for use in conferring overcharge protection in such batteries, such as lithium-ion batteries having a high-voltage cathode.

INTRODUCTION

The prevention of overcharge, a condition in which a cell's potential rises above the end-of-charge potential of its cathode, is important for achieving long lifetimes and averting catastrophic failure in lithium-ion batteries (LIBs).[1, 2] Batteries connected in series may be especially vulnerable to overcharge when mismatches in capacity occur. The condition may be forestalled by introducing additional external circuitry to monitor individual cell potentials in a battery pack, or by integrating internal safeguards to prevent undesirably high potentials from being reached.

One such approach involves incorporating additives into the battery electrolyte to mitigate excess applied current by shuttling charge between electrodes.[3, 4] These additives, called redox shuttles, oxidize at the cathode/electrolyte interface when the cell potential reaches the oxidation potential of the additive; then, after diffusing to the anode/electrolyte interface, they reduce back to the neutral form. Each cycle sees an electron transported from the anode to the cathode without shorting the cell.

Redox shuttles were first demonstrated as a protective mechanism in LIBs by Dahn and coworkers in 2005; the most successful early shuttles included derivatives of phenothiazine,[5] dialkoxybenzene,[3, 6, 7] 2,2,6,6-tetramethylpiperinyl oxide (TEMPO),[8] and triphenylamine.[9] In the decade since Dahn's initial reports, redox shuttles have enabled protection against overcharge for time periods equivalent to 300 or more charging cycles and at charging rates as high as 1C.[7, 10, 11]

Notable examples of redox shuttles that provide extensive overcharge protection at potentials appropriate for the commercially-utilized lithium iron phosphate (LFP) cathode include 1,4-di-tert-butyl-2,5-dimethoxybenzene,[3, 6, 7] 1,4-di-tert-butyl-2,5-bis(2-methoxyethoxy)benzene,[12] and a related imidazolium-functionalized ionic liquid salt.[13, 14] More recently, N-ethyl-3,7-bis(trifluoromethyl)phenothiazine (BCF3EPT) was reported as a highly soluble redox shuttle that provides extensive overcharge protection for the LFP cathode in LIBs, even at high charging rates.[10, 11, 15]

Despite the extensive overcharge protection capabilities observed for dimethoxybenzene and phenothiazine derivatives in LFP-based batteries, even at concentrations as low as 0.05 to 0.1 M, these compounds oxidize at potentials too low to be used with high-voltage cathodes like $LiMn_2O_4$ (LMO), $LiCoO_2$ (LCO), $LiNi_{1/3}Mn_{1/3}Co_{1/3}O_2$ (NMC), and $LiNi_{0.8}Co_{0.15}Al_{0.05}O_2$ (NCA). These cathode materials require redox shuttles that oxidize at potentials of at least 4.3 V vs. $Li^{+/0}$, as the end-of-charge potentials for LMO, NMC and NCA lie between 4.1 and 4.2 V.[16]

Dahn, Amine, and Zhang have reported redox shuttle candidates with oxidation potentials ranging from 4.0 to 4.8 V vs. $Li^{+/0}$, including 1,4-di-tert-butyl-2,5-bis(2,2,2-trifluoroethoxy)benzene,[17, 18] octafluoronaphthalene,[18] 2-methoxyhexafluoronaphthalene,[18] tetraethyl-1,4-di-tert-butyl-2,5-phenylene diphosphate,[19] and 1,4-bis(di-iso-propyl)phosphinyl)-2,5-dimethoxybenzene.[20] Although all five compounds protect high-voltage cathodes from overcharge, when paired with graphitic anodes, even the most robust shuttle is limited to a few dozen cycles of protection against 100% overcharge in LFP/graphite cells.

Accordingly, there remains a need in the art for compounds for use as redox shuttles, and batteries making use of such compounds, which effectively overcome the shortcomings of known compounds and batteries.

SUMMARY OF INVENTION

The presently-disclosed subject matter includes compounds that can be used as redox shuttles conferring overcharge protection. The presently-disclosed subject matter further includes rechargeable batteries, including rechargeable batteries having a high-voltage cathode, which include a redox shuttle, providing overcharge protection.

In some embodiments of the presently-disclosed subject matter, a compound is provided, which has the structure of formula I.

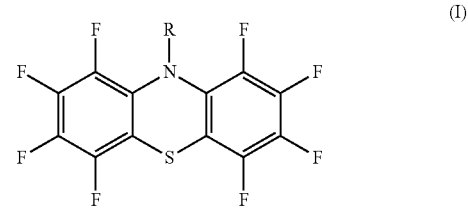

(I)

wherein R is selected from the group consisting of alkyl, aryl, alkylaryl, alkoxyaryl, alkylcarboxyl, aryl carbonyl, haloalkyl, perfluoroalkyl, glycols, haloaryl, a negative electrolyte, and a polymer.

In some embodiments, the compound has the structure of formula II.

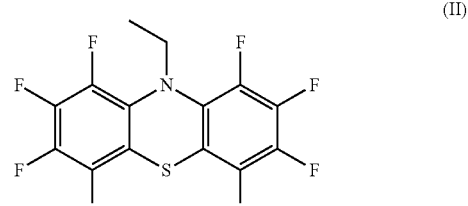

(II)

N-ethyl-1,2,3,4,6,7,8,9-octafluorophenothiazine (OFEPT)

In some embodiments, the compounds disclosed herein are included in a rechargeable battery comprising a negative electrode and a positive electrode. In some embodiments, the battery includes a high-voltage cathode and an anode. The high-voltage cathode can in some embodiments have an end-of-charge potential of about 4.0 V or greater. Exemplary high-voltage cathodes include LiFePO$_4$ (LFP), LiMn$_2$O$_4$ (LMO), LiCoO$_2$ (LCO), LiNi$_{1/3}$Mn$_{1/3}$Co$_{1/3}$O$_2$ (NMC), or LiNi$_{0.8}$Co$_{0.15}$Al$_{0.05}$O$_2$ (NCA). In some embodiments, the anode is graphitic. In some embodiments, the battery can include an electrolyte comprising a charge-carrying medium and a lithium salt.

In some embodiments the compounds disclosed herein are included in a battery at a concentration of about 0.05-0.1M. In some embodiments, the compound has a solubility of about 0.5M or greater. In some embodiments, the compound oxidizes at a potential of about 4.0 V to about 4.8V as compared to Li/Li+, at a potential of about 4.2V to about 4.5V, or at a potential of about 4.2V to about 4.3V.

In some embodiments, the battery comprises a positive electrode, a negative electrode, and an electrolyte. In some embodiments, the positive electrode is immersed in the electrolyte. In some embodiments, a battery comprising a passivating electrolyte additive, wherein the passivating electrolyte additive comprises the compound. In some embodiments, the battery can be selected from a lithium-ion battery and a sodium-ion battery. In some embodiments, the battery can comprise a photopolymerization initiator or photoredox catalyst, that includes the compounds disclosed herein. In some embodiments, electrode material includes the compounds disclosed herein. In some embodiments, the electrode material is included in a battery. In some embodiments, the battery is a non-aqueous redox flow battery. Articles including a battery as provided herein are also disclosed. Arrays comprising two or more batteries, including batteries connected in series are also disclosed.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
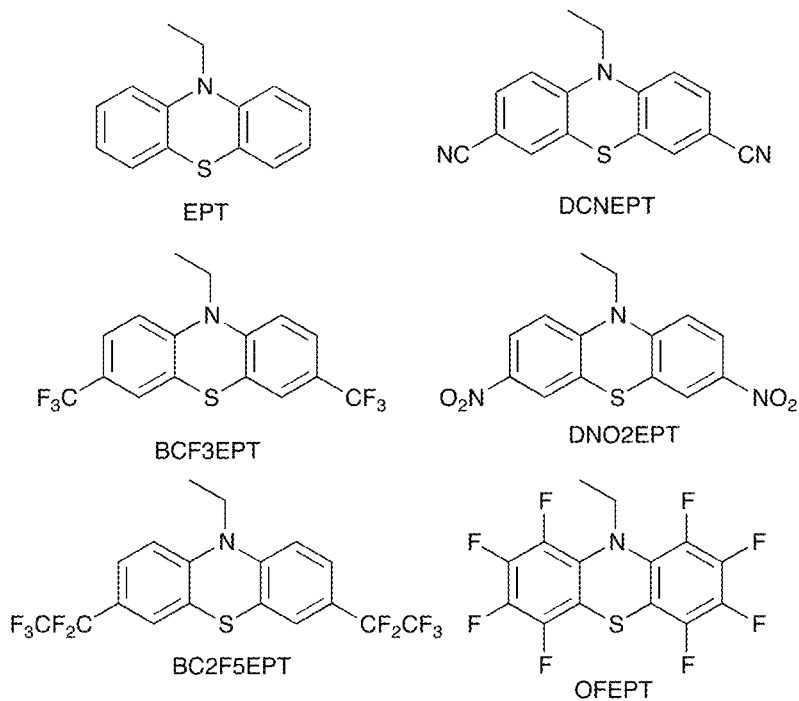
FIG. 1 provides chemical structures of N-ethylphenothiazine (EPT) and derivatives N-ethyl-3,7-bis(trifluoromethyl)phenothiazine (BCF3EPT), N-ethyl-3,7-bis(pentafluoroethyl)phenothiazine (BC2F5EPT), 3,7-dicyano-N-ethylphenothiazine (DCNEPT), N-ethyl-3,7-dinitrophenothiazine (DNO2EPT), and N-ethyl-1,2,3,4,6,7,8,9-octafluorophenothiazine (OFEPT).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds that can be used as redox shuttles conferring overcharge protection. The presently-disclosed subject matter further includes rechargeable batteries, including rechargeable batteries having a high-voltage cathode, which include a redox shuttle, providing overcharge protection.

In some embodiments of the presently-disclosed subject matter, a compound is provided, which has the structure of formula I.

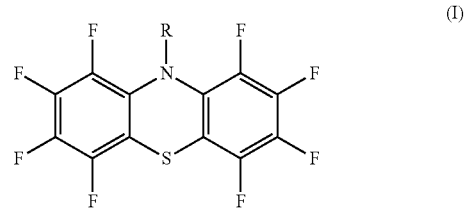

wherein R is selected from the group consisting of alkyl, aryl, alkylaryl, alkoxyaryl, alkylcarboxyl, aryl carbonyl, haloalkyl, perfluoroalkyl, glycols, haloaryl, a negative electrolyte, and a polymer.

In some embodiments, the compound has the structure of formula II.

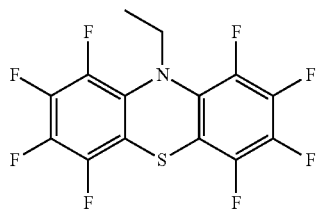

(II)

N-ethyl-1,2,3,4,6,7,8,9-octafluorophenothiazine (OFEPT)

In some embodiments, the compound can be used as a redox shuttle.

In some embodiments, the compound can be used as a passivating electrolyte additives for lithium-ion, sodium-ion, and other batteries.

In some embodiments, the compound can be used as a photopolymerization initiator or photoredox catalyst.

In some embodiments, the compound can be used as an electrode material in a battery including non-aqueous redox flow batteries.

As used here, the term "redox shuttle" refers to an electrochemically reversible compound that can become oxidized at a positive electrode of a battery, migrate to a negative electrode of the battery, become reduced at the negative electrode to reform the unoxidized/less-oxidized shuttle species, and migrate back to the positive electrode. A redox shuttle can be an electroactive compound, which can be heterocyclic. A redox shuttle can protect against overcharging.

The presently-disclosed subject matter includes a rechargeable battery. In some embodiments, the rechargeable battery includes a negative electrode, a positive electrode, and an electrolyte that includes a compound as disclosed herein, e.g., OFEPT. In some embodiments, the positive electrode is immersed in the electrolyte. In some embodiments, the electrolyte further comprises a charge-carrying medium and a lithium salt.

In some embodiments, the rechargeable battery is a rechargeable lithium-ion battery, which includes a high-voltage cathode, a negative electrode, an electrolyte comprising a charge-carrying medium and a lithium salt, and a redox shuttle comprising a compound as disclosed herein.

The term "electrolyte" is well understood to those of ordinary skill in the art and provides a charge-carrying pathway between the negative electrode and the positive electrode. The electrolyte can include a charge-carrying medium and a lithium salt. The electrolyte can also include a redox shuttle.

In some embodiments, the battery makes use of a compound/redox shuttle at a concentration of about 0.05-0.1M. In some embodiments, the battery makes use of a compound/redox shuttle having a solubility of about 0.5M or greater.

The term "negative electrode" is well understood to those of ordinary skill in the art and refers to one of a pair of electrodes that, under normal circumstances and when the battery/cell is fully charged, has the lowest potential. The negative electrode that can be used in connection with the presently-disclosed subject matter is not particularly limited and can be generally selected from those known in the art, for example, a graphitic anode.

The term "positive electrode" is well understood to those of ordinary skill in the art and refers to one of a pair of electrodes that, under typical circumstances, and when the battery/cell is fully charged, will have the highest potential that it can achieve under normal operation.

As noted herein, the presently-disclosed subject matter includes rechargeable batteries in which the positive electrode is a high-voltage cathode. Examples of high-voltage cathodes include, but are not limited to $LiFePO_4$ (LFP), $LiMn_2O_4$ (LMO), $LiCoO_2$ (LCO), $LiNi_{1/3}Mn_{1/3}Co_{1/3}O_2$ (NMC), and $LiNi_{0.8}Co_{0.15}Al_{0.05}O_2$ (NCA). A high-voltage cathode is one that can be said to have an end-of-charge potential of about 4.0 V or greater. Such high-voltage cathodes benefit from redox shuttles that oxidize at potentials of at least about 4.0, 4.1, 4.2, 4.3, 4.4, 4.5, 4.6, or 4.7 to about 4.8 V as compared to $Li/Li^+$.

In some embodiments of the presently-disclosed subject matter, the battery makes use of a compound that oxidizes at a potential of about 4.0 V to about 4.8V as compared to $Li/Li^+$. In some embodiments, the compound oxidizes at a potential of about 4.2V to about 4.5V. In some embodiments, the compound oxidizes at a potential of about 4.2V to about 4.3V.

The presently-disclosed subject matter is further inclusive of an article that includes a battery as disclosed herein.

Batteries connected in series can be particularly vulnerable to overcharge. The presently-disclosed subject matter is inclusive of an array that includes two or more batteries as disclosed herein. In some embodiments, the array includes two or more batteries connected in a series.

While the terms used herein are believed to be well understood by those of ordinary skill in the art, certain definitions are set forth to facilitate explanation of the presently-disclosed subject matter.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyl s such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Preferably, an alkyl group comprises from 1 to 20 carbon atoms, more preferably, from 1 to 10 carbon atoms. While alkyl is generally used to refer to both unsubstituted alkyl groups and substituted alkyl groups; however, substituted alkyl groups are also specifically referred to herein by identifying the specific substituent(s) on the alkyl group. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A lower alkyl group is an alkyl group containing from one to six (e.g., from one to four) carbon atoms.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, between 6 to 12 carbon atoms. The term aryl also includes heteroaryl, which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term non-heteroaryl, defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

"Alkylaryl" refers to an acyclic alkyl in which one of the hydrogen atoms bonded to a carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is $(C_6-C_{30})$ arylalkyl, e.g., the alkanyl, alkenyl or alkynyl moiety of the arylalkyl group is $(C_1-C_{10})$ and the aryl moiety is $(C_6-C_{20})$, more preferably, an arylalkyl group is $(C_6-C_{20})$ arylalkyl, e.g., the alkanyl, alkenyl or alkynyl moiety of the arylalkyl group is $(C_1-C_8)$ and the aryl moiety is $(C_6-C_{12})$.

"Alkoxyaryl" refers to an —O-arylalkyl where arylalkyl is as defined herein.

"Alkylcarboxyl" means a —C(O)R group where R is alkyl, as defined herein.

"Arylcarbonyl" refers to a —C(O)-aryl where aryl is as defined herein.

"Halogen" or "halo" refers to the halogens fluorine, chlorine, bromine and iodine. Thus, a haloalkyl, refers to an alkyl group substituted with one or more halogens. A halo aryl refers to an aryl group substituted with one or more halogens.

"Perfluoroalkyl" refers to alkyl groups in which essentially all of the carbon-bonded hydrogen has been replaced by fluorine.

Glycols include alcohols in which at least two hydroxyl groups are attached to different carbon atoms in an organic compound, including alkylene glycols such as ethylene glycol and propylene glycol.

A polymer consists of a large number of repeating units bonded together. The term "polymer," when used herein to refer to R of the compounds disclosed herein, includes vinyl polymers, including but not limited to ethylene, propylene, and styryl polymers, cyclic alkenes, including for example norbornene, norbornadiene, cyclopentene, and cyclooctatetraene, acrylates, amines, epoxies, isocyanates, and the like. Also, as used herein, polymer refers to linear polymers as well as other arrangements, including for example, dendrimer, star, and hyper branched polymers. In some embodiments, the polymer can include phenothiazine as the sole monomer in a repeating polymer. In some embodiments, the polymer can include phenothiazine as part of a polymer that contains more than one repeat unit, e.g., alternating copolymer or block copolymer.

As used herein, a redox shuttle is a compound that mitigates excess charge by shuttling electronic charge between electrodes in a battery. In particular, the redox shuttle oxidizes at the cathode/electrolyte interface when the cell potential reaches the oxidation potential of the additive; then, after diffusing to the anode/electrolyte interface, they reduce back to the neutral form.

A charge-carrying medium is any composition, material, or particle that carries electric charges.

A passivating electrolyte additive is a composition added that can stabilize the surface of an anode, typically by forming a passivation film.

A photopolymerization initiator is a chemical species that upon exposure to light (for example, ultraviolet or visible spectrum) produces a reactive species that can react with a composition, and changes the composition in one or more properties. An exemplary photopolymerization initiator can, for example, upon exposure to light, react with a polymerizable composition to generate a cross-linked polymer.

A photoredox catalyst uses light to facilitate a chemical reaction by mediating a transfer of electrons between chemical compounds. The photoinduction of electron transfer of the catalysts allows for the activation of substrates that do not readily absorb the energy of light by themselves.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC Nomenclature.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Figure 2:
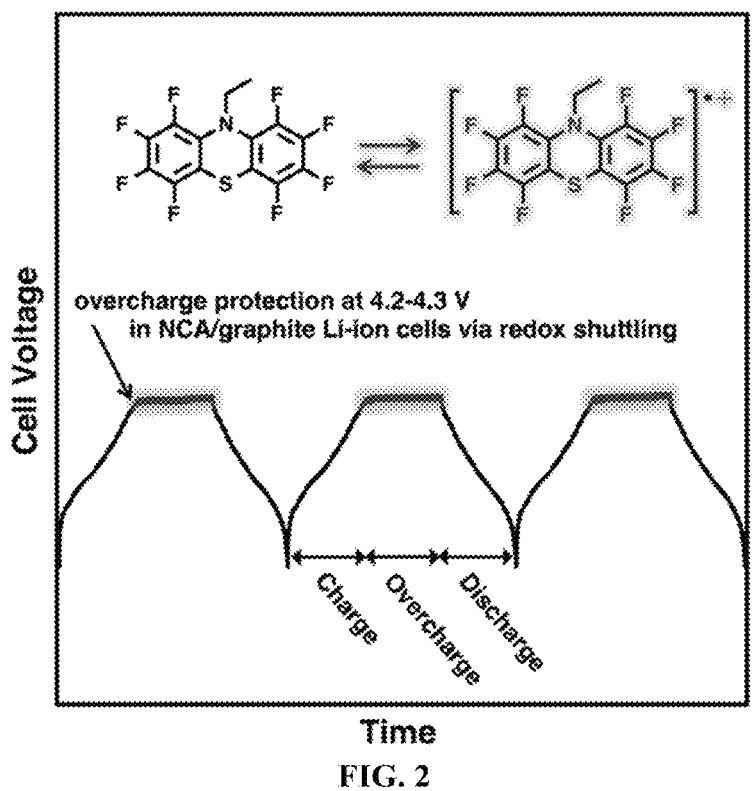
FIG. 2 depicts how an exemplary fluorinated phenothiazine derivative mitigates excess current in an overcharging lithium-ion cell containing a high-voltage cathode by shuttling it through the electrolyte in redox reactions as the electrode/electrolyte interfaces.

As explained by the present inventors in more details in these Examples, they synthesized three new phenothiazine derivatives with electron-withdrawing substituents. Of these compounds, the perfluorinated shuttle candidate OFEPT (FIG. 2), exhibited a reversible oxidation at 4.3 V vs. $Li^{+/0}$, making it the first phenothiazine derivative appropriate for overcharge protection for higher-voltage cathodes such as NCA cathodes. Furthermore, this is the first instance of overcharge protection of NCA-containing cells through the use of redox shuttle additives.

Example 1

Recent work with phenothiazine-based redox shuttles led to the development of stable materials with a variety of oxidation potentials. The derivatives with the highest oxidation potentials are 3,7-disubstituted derivatives of N-ethylphenothiazine (EPT) containing trifluoromethyl (BCF3EPT) or cyano (DCNEPT) groups, with oxidation potentials of 3.83 and 3.90 V vs. $Li^{+/0}$, respectively (FIG. 1, Table 1).

TABLE 1

Calculated adiabatic IPs, and half-wave oxidation ($E_{1/2}^{+/0}$) and peak values of the potential of the forward wave of first reduction events ($E_p^{0/-}$) for EPT, 3,7-disubstituted EPT derivatives, and OFEPT vs. $Li^{+/0}$ at 0 V.

| Compound | Calculated adiabatic IP (eV) [a] | $E_{1/2}^{+/0}$ vs. $Li^{+/0}$ (V) [b] | $E_p^{0/-}$ vs. $Li^{+/0}$ (V) [b] |
|---|---|---|---|
| EPT | 6.48 | 3.51 | N/A |
| BCF3EPT | 6.91 | 3.83 | N/A |
| BC2F5EPT | 7.06 | 3.86 | N/A |
| DCNEPT | 7.30 | 3.90 | 0.76 [c] |
| DNO2EPT | 7.50 | 3.97 | 2.39 [c] |
| OFEPT | 7.55 | 4.30 | 0.52 [c] |

[a] adiabatic IPs calculated at the B3LYP/6-311G(d,p) level of theory,
[b] potentials of redox events obtained from cyclic voltammograms recorded in 1.2M $LiPF_6$ in EC/EMC (3:7 wt. ratio) at 100 mv/s.
[c] denotes that the event was irreversible.

Attempting to achieve overcharge protection at higher potentials, redox shuttles were synthesized with less electron-rich cores (phenoxazine and carbazole) but it was found that these compounds failed earlier in overcharge tests than their phenothiazine-based counterparts. Introduction of electron-withdrawing substituents at the N and S positions likewise increased oxidation potentials but yielded less stable radical cations with correspondingly limited overcharge protection capability. From these results, it was believed important to retain the electron-rich phenothiazine core and stable N substituents (ethyl, iso-propyl, phenyl), and instead focus on varying the substituents on the aromatic carbon atoms of the phenothiazine ring. Thus, attaining stable phenothiazine derivatives for high-voltage overcharge protection by exploring perfluoroalkyl, nitro, or perfluoro substitution of the aromatic periphery was conducted. Herein is disclosed the synthesis and characterization of the following redox shuttle candidates explored as redox shuttle candidates that operate at above>4 V vs. $Li^{+/0}$ for overcharge protection of high-votage cathodes: N-ethyl-3,7-bis(pentafluoroethyl)phenothiazine (BC2F5EPT), N-ethyl-3,7-dinitrophenothiazine (DNO2EPT), and N-ethyl-1,2,3,4,6,7,8,9-octafluorophenothiazine (OFEPT) (FIG. 1).

The structures of the new derivatives were inspired by the results of density functional theory (DFT) calculations, which were used to compute adiabatic ionization potentials (IPs). A good correlation was found between calculated adiabatic IPs and oxidation potentials for previously-reported phenothiazine derivatives, and use has since been made of the hybrid B3LYP density functional in conjunction with the 6-311G(d,p) basis set to predict these values prior to synthesis.[25] The results of calculations for new candidates are summarized in Table 1, along with adiabatic IPs for previously reported EPT, BCF3EPT, and DCNEPT at the same level of theory.

The results of the DFT calculations suggest that BC2F5EPT would oxidize at a potential higher than BCF3EPT ($E_{1/2}^{+/0}$=3.83 V vs. $L^{+/0}$) but lower than DCNEPT ($E_{1/2}^{+/0}$=3.90 V), and that both DNO2EPT and OFEPT would oxidize at potentials higher than DCNEPT. Although DNO2EPT and OFEPT were of interest for high-voltage applications, it was noted that BC2F5EPT might be practical for protection of LFP-based batteries or for other applications requiring stable electro-active materials. In addition to overcharge protection, highly stable electro-active species such as those listed above are of interest for use in non-aqueous RFBs, lithium-air batteries, and photo-redox catalysis. Therefore, all three compounds were synthesized with the expectation that DNO2EPT and OFEPT would be the most promising candidates for high-voltage overcharge protection.

DNO2EPT and BC2F5EPT were synthesized from phenothiazine in two and three steps respectively, as shown in Scheme 1.

pentafluorophenylthiol via treatment with $Cu_2O$. The resulting copper complex and aryl bromide reacted to form a thioether bridging two fluorinated phenyl rings, one of which contained a primary amine at the position ortho to S. The phenothiazine ring was closed upon deprotonation of the aniline, reacting the amide ion with an $sp_2$-hybridized C

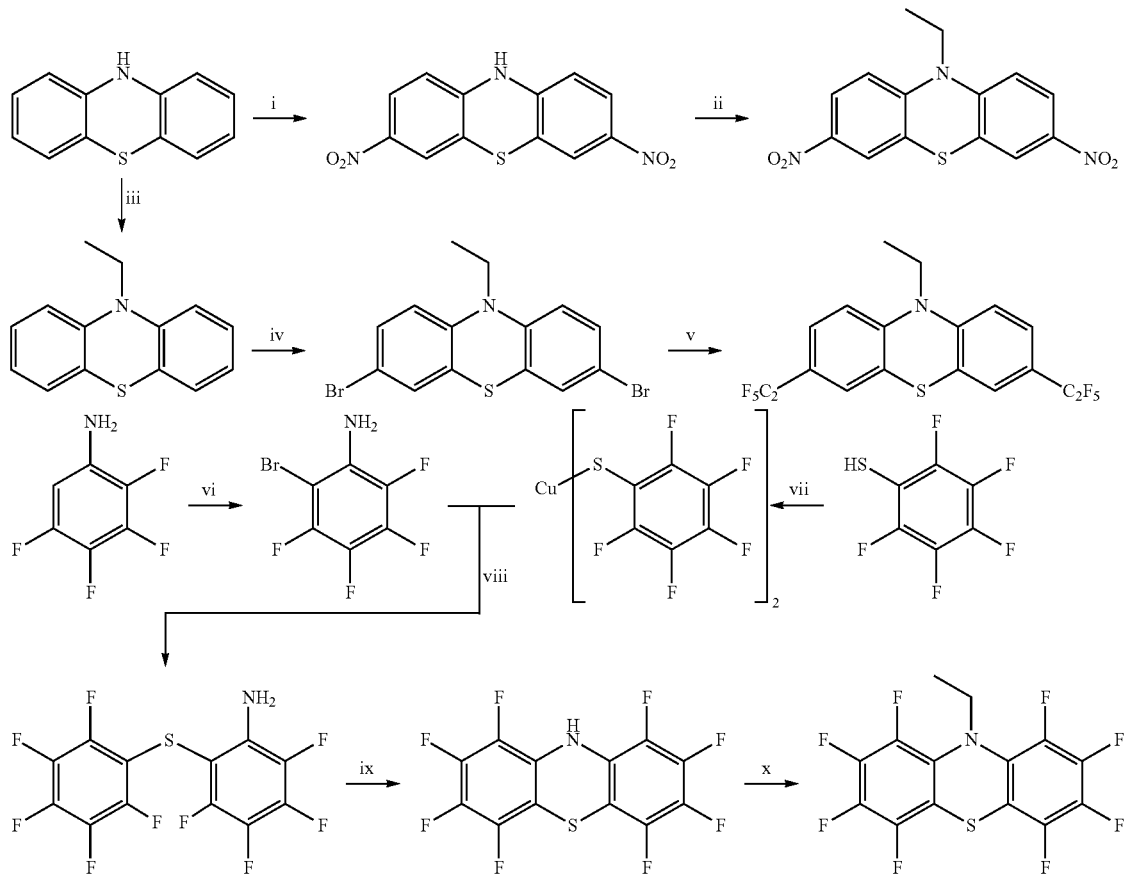

Scheme 1. Synthetic routes to obtain DNO2EPT, BC2F5EPT, and OFEPT.

Reagents: (i) $NaNO_2$, AcOH, $CHCl_3$, rt, 1 h, (ii) NaH, DMF, EtBr, 60° C., 6 h, (iii) NaH, DMF, EtBr, 60° C., 6 h, (iv) NBS, DMF, o/n, (v) $NaOCOC_2F_5$, CuI, NMP, 180° C., 2 days, (vi) Fe, NaOAc, AcOH, $Br_2$, 50° C., 3 h, (vii) $Cu_2O$, ethanol, reflux, 5 h, (viii) anhydrous DMF, reflux, 2 h, (ix) NaH, anhydrous dioxane, reflux, 4 h, and (x) NaH, DMF, EtBr, 60° C., 12 h.

To prepare DNO2EPT, phenothiazine was doubly nitrated with sodium nitrate in acetic acid following a procedure previously reported in *Chem. Heterocycl. Compd.*, 32:365-70 (1996); deprotonation of the product and treatment with bromoethane afforded the desired redox shuttle candidate. To synthesize BC2F5EPT, phenothiazine was deprotonated with sodium hydride and added bromoethane to alkylate the N position, yielding EPT; dibromination of the product was performed using N-bromosuccinimide as previously reported in *Chem. Comm.* 50: 5339-5341 (2014). The dibrominated product was then treated with sodium pentafluoropropionate under conditions similar to those employed in our previous synthesis of BCF3EPT to afford BC2F5EPT.

OFEPT was prepared in a convergent, multi-step synthesis in which the phenothiazine core was built from fluorinated benzene derivatives, as shown in Scheme 1. 2,3,4,5-Tetrafluoroaniline was brominated, and the product was combined with bis(2,3,4,5,6-pentafluorothiophenolate) copper(II), the latter of which was prepared from 2,3,4,5,6- atom ortho to S on an adjacent ring.[34, 35] Lastly, an alkylation reaction afforded OFEPT. Detailed procedures and structural characterization of all three redox shuttle candidates are provided herein.

Figure 3:
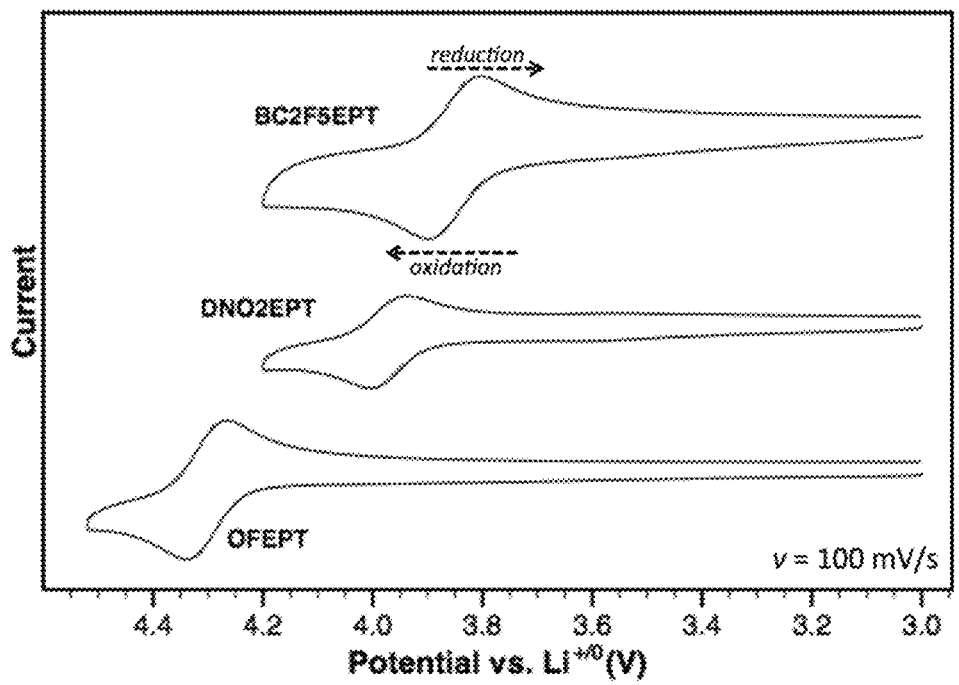
FIG. 3 includes cyclic voltammograms of BC2F5EPT, DNO2EPT, and OFEPT at ca. 0.3 mM in 1.2 M LiPF$_6$ in EC/EMC (3:7 wt. ratio) at a scan rate of 100 mV/s with a glassy carbon working electrode, Pt wire counter electrode, and Li foil reference electrode.
Figure 4:
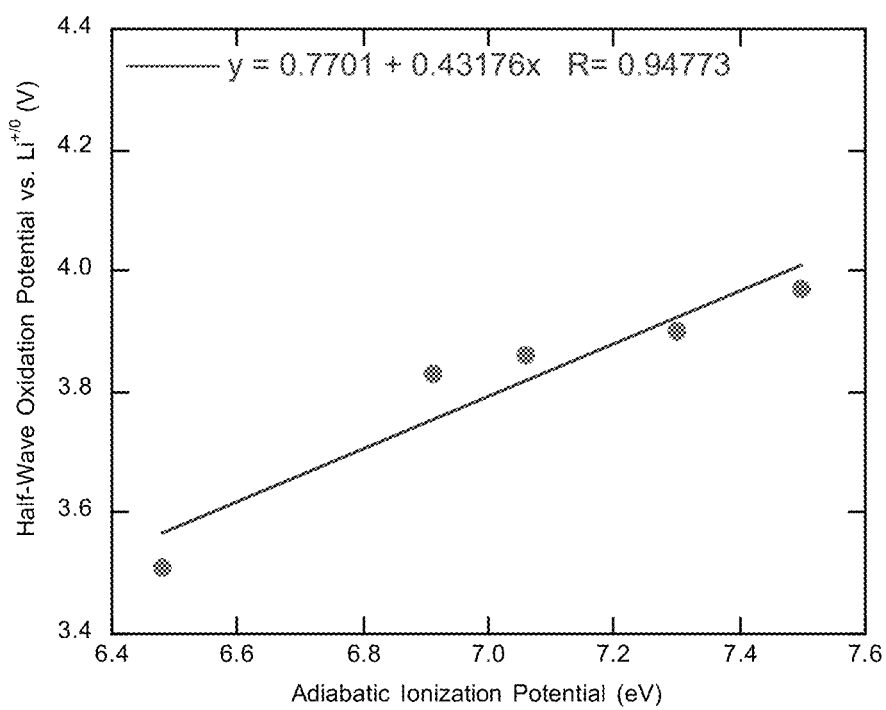
FIG. 4 includes a plot of half-wave oxidation potentials for the first oxidation event for redox shuttle candidates EPT, BCF3EPT, BC2F5EPT, DCNEPT, and DNO2EPT in 1.2 M LiPF$_6$ in EC/EMC (3:7 wt. ratio) recorded at a scan rate of 100 mV/sec vs. the adiabatic IPs calculated at the B3LYP/6-311G(d,p) level of theory.
Figure 5:
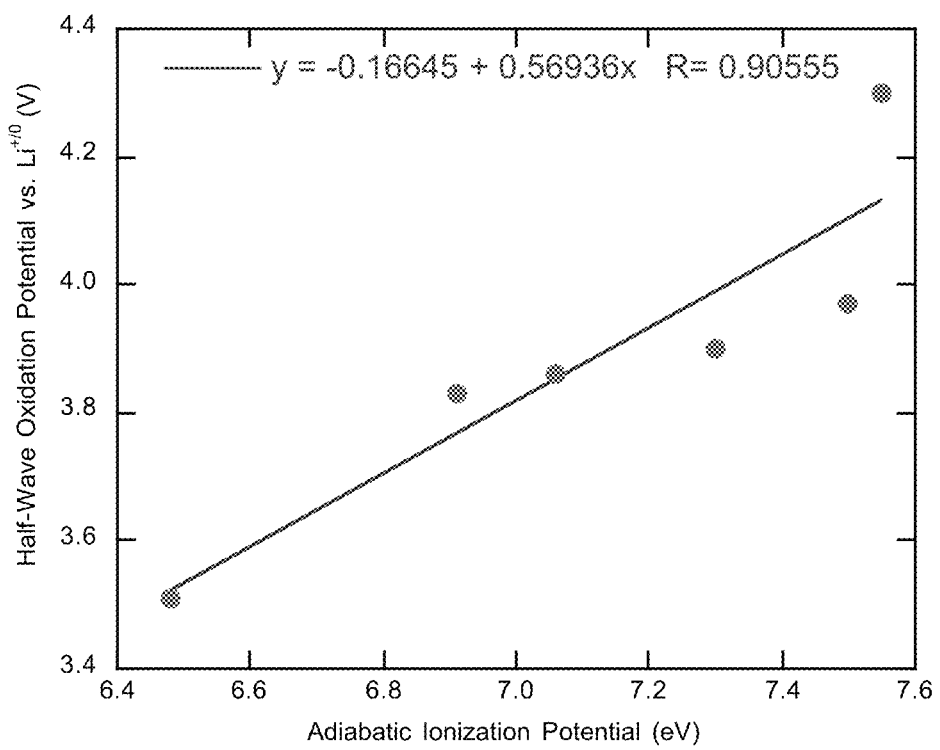
FIG. 5 includes a plot of half-wave oxidation potentials for the first oxidation event for redox shuttle candidates EPT, BCF3EPT, BC2F5EPT, DCNEPT, DNO2EPT, and OFEPT in 1.2 M LiPF$_6$ in EC/EMC (3:7 wt. ratio) recorded at a scan rate of 100 mV/sec vs. the adiabatic IPs calculated at the B3LYP/6-311G(d,p) level of theory.

Electrochemical potentials were measured and analyzed the reversibility of redox events using cyclic voltammetry (CV) in 1.2 M $LiPF_6$ in ethylene carbonate/ethylmethyl carbonate (EC/EMC, 3:7 wt. ratio). CV experiments of redox shuttle candidates BC2F5EPT, DNO2EPT, and OFEPT revealed reversible first oxidation events at 3.86, 3.97, and 4.30 V, respectively, vs. $Li^{+/0}$ (FIG. 3). The correlation between calculated adiabatic IPs and first oxidation potentials was generally good for EPT and the 3,7-disubstituted derivatives shown in FIG. 1, affording an $R^2$ value of 0.947 for the line of best fit (FIG. 4). The oxidation potential of OFEPT was higher than expected from the trend exhibited by the 3,7-disubstituted derivatives, and a lower $R^2$ value (0.906) results when OFEPT is included (FIG. 5).

Figures 6A, 6B, 6C, 6D, 6E, 6F:
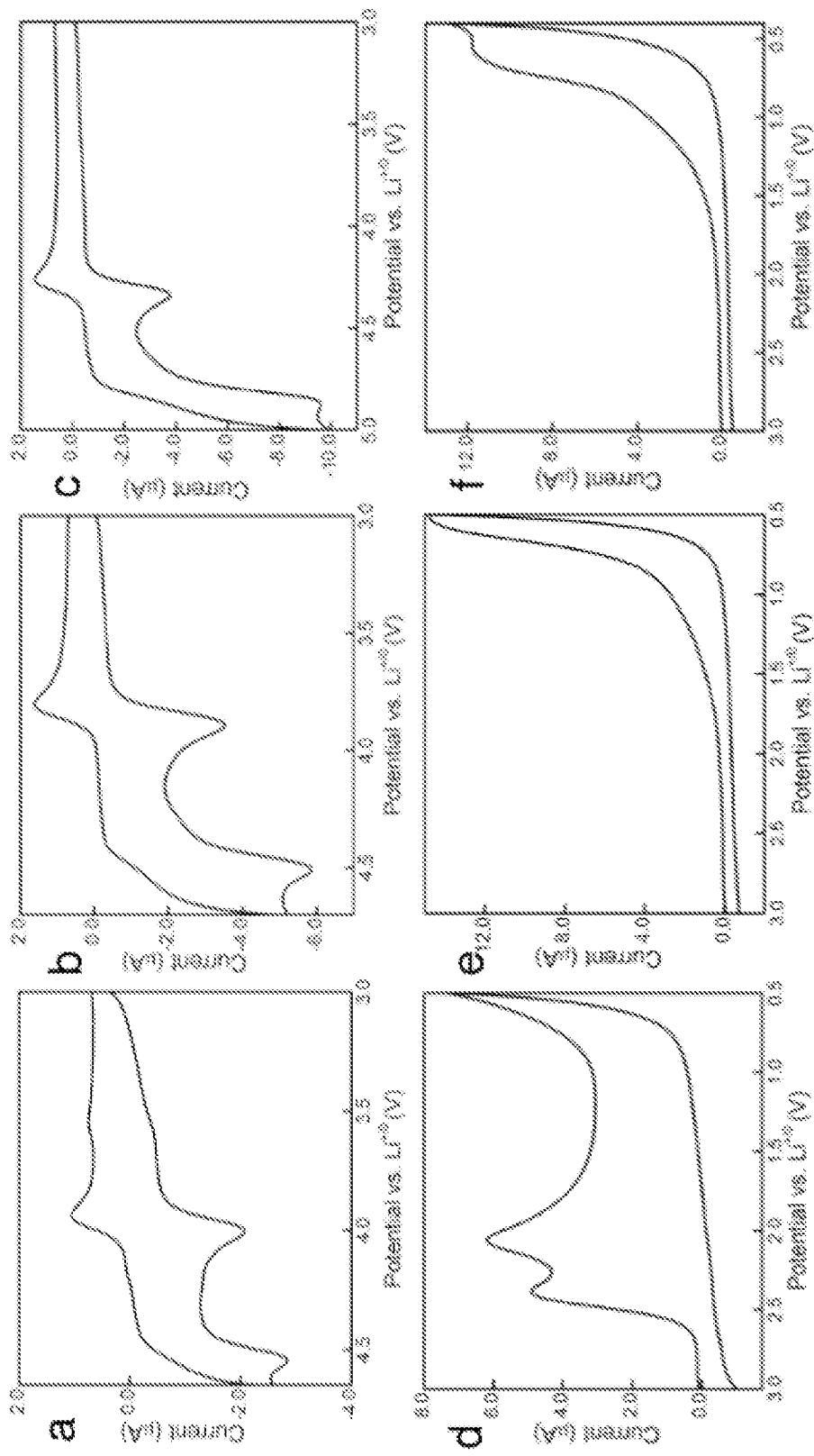
FIGS. 6a-6f include cyclic voltammograms of DNO2EPT (a,d), BC2F5EPT (b,e), and OFEPT (c,f) at 0.3 mM in 1.2 M LiPF$_6$ in EC/EMC (3:7 wt. ratio) recorded at a scan rate of 100 mV/sec showing irreversible second oxidations in some cases (a, b, and c) and irreversible reductions in others (d, e, and f).

CV experiments were also performed over a wider electrochemical window (0.4-5.0 V, FIG. 6). First an electrochemical window of 3.0-5.0 V (higher) was scanned, looking for oxidation events and then from 3.0-0.4 V (lower) looking for reduction events. Scanning to higher potentials revealed that all compounds display an irreversible second oxidation at or above 4.5 V. Scanning to lower potentials leads to cathodic currents produced from reduction of DNO2EPT and OFEPT. For DNO2EPT, irreversible reduction events were observed at 2.39 and 2.06 V. For OFEPT, an irreversible reduction was observed at 0.52 V. The high reduction potential of DNO2EPT suggests that its use in LIBs containing graphitic electrodes would be impractical because reduction of the neutral compound to the radical anion would occur during charging, leading to decomposition of the redox shuttle and/or limiting charging potential. Reduction of OFEPT during charging is also a possibility, but precedence suggests that it may not be detrimental to performance: in a prior study, we found a redox shuttle with a low-potential reduction event that nonetheless exhibited a faculty for overcharge protection in LIB coin cells containing graphitic electrodes.[21]

Overcharge tests in coin cell batteries in which redox shuttles were cycled at 100% overcharge were performed. Under this procedure, 200% of the current needed to reach the end-of-charge potential of the cathode is applied, following which the cell is discharged. This cycle of charge-overcharge-discharge is repeated until the redox shuttle can no longer mitigate current and the cell potential rises to 5 V. In these experiments, in the first 200% charge cycle, only a few hours are spent in overcharge due to the longer time required to reach the shuttle potential as a result of SEI formation. Starting in the second cycle, the cells spend ca. 10 h in charge, 10 h in overcharge, and 10 h in discharge.

Figure 7:
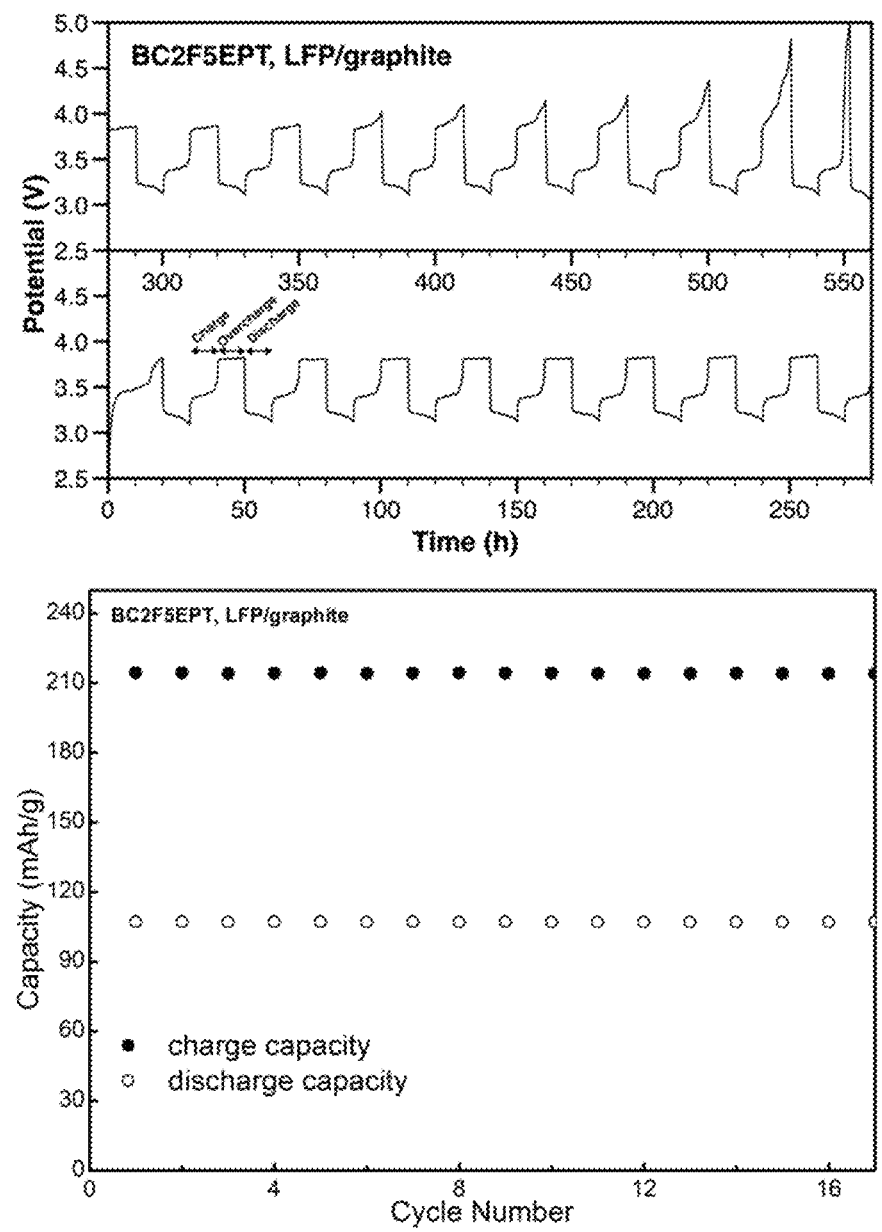
FIG. 7 includes plots of Potential vs. time (top) and capacity vs. cycle number (bottom) for 100% overcharge cycling of BC2FEPT in LFP/graphite coin cells. BC2FEPT was incorporated into 1.2 M LiPF$_6$ in EC/EMC (3:7 wt. ratio) at 0.08 M; 100% overcharge cycling was performed at a rate of C/10.

For overcharge protection when high voltage cathodes are used, OFEPT was the only viable redox shuttle candidate; both BC2F5EPT and DNO2EPT are too easily oxidized. For these systems, overcharge tests were performed instead with LFP/graphite cells, though DNO2EPT's performance could not be studied due to its limited solubility. By contrast, BC2F5EPT is highly soluble, dissolving at 1 M (30 wt. %) in carbonate-based electrolytes. In these initial cycling tests, BC2F5EPT's performance was unremarkable for an LFP shuttle, surviving a mere 17 cycles of 100% overcharge cycling before reaching 5 V (FIG. 7). Perhaps a different shuttle concentration or electrolyte environment could lead to more extensive cycling.

Figure 8:
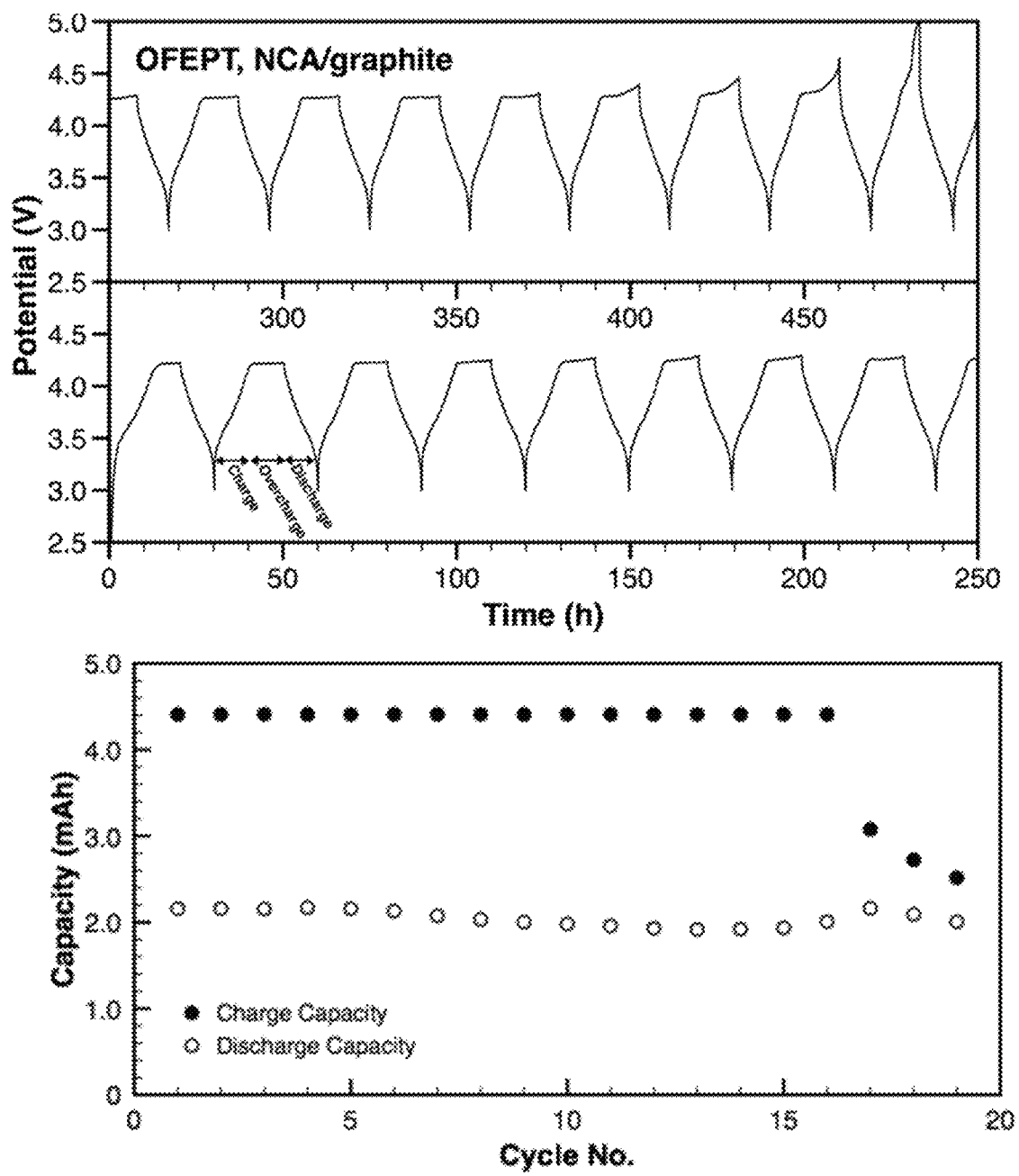
FIG. 8 includes plots of Potential vs. time (top) for 100% overcharge cycling of OFEPT in NCA/graphite coin cells. OFEPT was incorporated into 1.2 M LiPF$_6$ in EC/EMC (3:7 wt. ratio) at 0.08 M; 100% overcharge cycling was performed at a rate of C/10; and charge and discharge capacities vs. cycle number (bottom) for the same cell.

Ultimately interest lies in achieving overcharge protection when high-voltage cathodes such as LMO, LCO, NMC, and NCA are used in LIBs. To test overcharge performance, NCA/graphite coin cells were used. OFEPT's oxidation potential of 4.30 V is ideal for NCA cathodes, and the compound readily dissolves at 0.5 M (13 wt. %) in carbonate-based electrolytes. Here we cycled NCA/graphite coin cells containing OFEPT at 0.08 M for consistency with previous redox shuttle studies. The overcharge cycling results for OFEPT in an NCA/graphite coin cell are shown in FIG. 8. Here OFEPT was observed to protect cells from overcharge at potentials ranging from 4.2-4.3 V, demonstrating the first example of a phenothiazine derivative that protects a high-voltage cathode from overcharge.

During cycling, the discharge capacity decreased by 7%; the decrease in charge capacity is equalized by increased overcharge protection, perhaps due to the effect of the abusive cycling conditions on electrode stability. Hence the cell capacity faded slowly upon extended cycling in the case of OFEPT. In the 14$^{th}$ overcharge cycle, the potential of the cell during overcharge began to increase at the end of the cycle. This effect became more pronounced in each subsequent cycle, although the cell potential does not reach 5 V until cycle 17. Although the lifetime for protection is short compared to BCF3EPT and other shuttles used with LFP-containing cells, this performance is in line with recently reported dimethoxybenzene-based redox shuttles used in LiMn$_2$O$_4$/Li and LiMn$_2$O$_4$/MCMB coin cells.[19, 20]

In summary, three new phenothiazine derivatives were synthesized with electron-withdrawing substituents. Of these compounds, the perfluorinated shuttle candidate OFEPT exhibited a reversible oxidation at 4.3 V vs. Li$^{+/0}$, making it the first phenothiazine derivative appropriate for overcharge protection for higher-voltage cathodes such as NCA cathodes. Furthermore, it seems this is the first example of overcharge protection of NCA-containing cells through the use of redox shuttle additives.

Example 2: Synthesis and Characterization

Overall Experimental

Bromoethane, copper(I) oxide, bromine, anhydrous N,N-dimethylformamide (DMF), N-methyl-2-pyrrolidone (NMP), charcoal, and 1,4-dioxane were purchased from Sigma Aldrich. Phenothiazine and copper iodide were obtained from Acros Organics. Sodium hydride, sodium acetate, and acetic acid were purchased from Alfa Aesar. Pentafluorothiophenol and sodium pentafluoropropionate were purchased from Oakwood Chemical, iron powder from Mallinckrodt Pharmaceuticals, 2,3,4,5-tetrafluoroaniline from AK Scientific, potassium hydroxide and celite from Fisher Scientific, and ethanol from Decon Labs. All reagents were used without further purification.

Silica gel (65×250 mesh) was purchased from Sorbent Technologies, and solvents for purification were purchased from VWR International. $^1$H, $^{19}$F and $^{13}$C NMR spectra were obtained on 400 MHz Varian NMR spectrometers in DMSO-d$_6$, acetone-d$_6$ or CDCl$_3$ purchased from Cambridge Isotope Laboratories. $^{19}$F NMR spectra were recorded in CDCl$_3$ using hexafluorobenzene (Alfa Aesar) as an internal standard, and the chemical shifts are reported vs. CFCl$_3$ at 0 ppm by adjusting the shift of hexafluorobenzene to −164.9 ppm. Mass spectra were obtained on an Agilent 5973 Network mass-selective detector attached to Agilent 6890N Network GC system. Elemental analyses were performed by Atlantic Microlab, Inc.

Synthesis of DNO2EPT, BC2F5EPT, and OFEPT

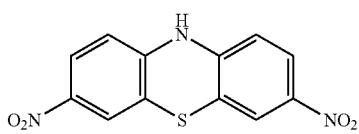 [SMILES: O=[N+]([O-])c1ccc2c(c1)Sc1cc([N+](=O)[O-])ccc1N2]

3,7-Dinitrophenothiazine

Glacial acetic acid (2 mL) was added to a suspension of phenothiazine (2.00 g, 10.1 mmol) in chloroform (10 mL) in a 100 mL round-bottomed flask containing a stir bar. Sodium nitrite (2.80 g, 40.6 mmol) was added to the reaction mixture in multiple portions over 20 min, after which more glacial acetic acid (4 mL) was added in order to maintain vigorous stirring. After 1 h, the reaction mixture was filtered to isolate the product as a red solid, which was washed with chloroform and air-dried. The isolated red solid (1.33 g) was largely insoluble in most organic solvents. $^1$H NMR of the crude product in DMSO-$d_6$ is consistent with the formation of the desired dinitrated product with ca. 10% of mononitrated product. The crude product was used without purification in the next step. Major product: $^1$H NMR (400 MHz, DMSO-$d_6$) δ 7.85 (dd, J=2.0 Hz, 8.4 Hz, 2H), 7.74 (d, J=2.4 Hz, 2H), 6.72 (d, J=9.2 Hz, 2H).

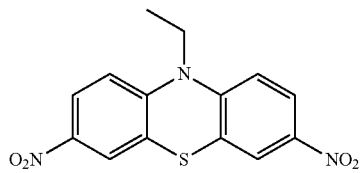 [SMILES: CCN1c2ccc([N+](=O)[O-])cc2Sc2cc([N+](=O)[O-])ccc21]

N-Ethyl-3,7-dinitrophenothiazine

Crude 3,7-dinitrophenothiazine (1.33 g, 4.58 mmol) was dissolved in anhydrous DMF (50 mL) in a 250 mL round-bottomed flask containing a stir bar, which was then fitted with a rubber septum under dry N$_2$. Sodium hydride (60% dispersion in mineral oil, 0.301 g, 7.50 mmol) was added at rt, upon which the solution became green in color. Bromoethane (2.4 mL, 33 mmol) was added to the reaction mixture, and the reaction flask was immersed in an oil bath and heated to 60° C. The reaction mixture was stirred for 6 h before the reaction flask was removed from the oil bath. The mixture was then allowed to cool to rt and was diluted with water to precipitate the crude product. The crude material was purified by column chromatography with silica gel, eluting with ethyl acetate/hexanes (1:4) to afford 0.296 g (9% over 2 steps) of the desired compound as a red solid. $^1$H NMR (400 MHz, acetone-$d_6$) δ 8.52-8.55 (m, 2H), 8.41 (m, 2H), 7.72-7.74 (m, 2H), 4.65 (q, J=6.4 Hz, 2H), 1.91 (t, J=6.8 Hz, 3H). $^{13}$C NMR (100 MHz, acetone-$d_6$) δ 150.1, 145.0, 125.5, 124.6, 123.6, 117.2, 44.6, 13.3. GCMS: m/z 317 (100%), 302 (17%), 288 (68%), 271 (17%), 242 (35%), 225 (14%), 196 (32%). Anal. calcd. for $C_{14}H_{11}N_3O_4S$ C, 52.99; H, 3.49; N, 13.24. Found C, 52.68; H, 3.36; N, 12.77.

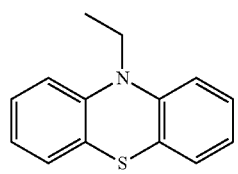 [SMILES: CCN1c2ccccc2Sc2ccccc21]

N-Ethylphenothiazine

This compound was prepared from phenothiazine as previously described.[11]

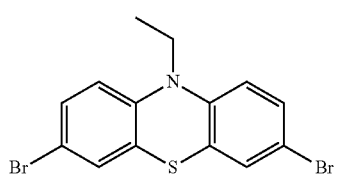 [SMILES: CCN1c2ccc(Br)cc2Sc2cc(Br)ccc21]

3,7-Dibromo-N-ethylphenothiazine

This compound was prepared from N-ethylphenothiazine as previously described.[11]

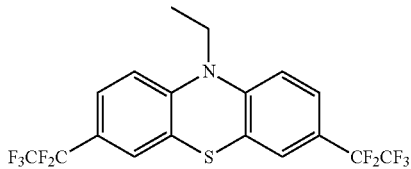

N-Ethyl-3,7-bis(pentafluoroethyl)phenothiazine 3,7-Dibromo-N-ethyl-phenothiazine (0.387 g, 1.00 mmol), copper (I) iodide (1.33 g, 7.01 mmol), and sodium pentafluoropropionate (0.745 g, 4.05 mmol) were dissolved in anhydrous NMP (10 mL) in a 100 mL round-bottomed flask containing a stir bar and fitted with a rubber septum. The reaction mixture was sparged with N$_2$ for 15 min as the reaction flask was immersed in an oil path programmed to heat to 150° C. The reaction mixture was stirred under N$_2$ at 150° C. for 48 h. Upon completion, the reaction flask was removed from the oil bath and allowed to cool to rt. The reaction mixture was poured into a mixture of hexane and celite and then filtered to remove solids. The filtrate was then washed with brine, dried over MgSO$_4$, and filtered again to remove solids. The crude product concentrated by rotary evaporation and was purified by column chromatography with silica gel using 100% hexanes, which afforded 0.205 g (45%) of the desired product as a yellow oil. $^1$H NMR (400 MHz, CDCl$_3$) δ 7.36 (dd, J=1.6, 8.4 Hz, 2H), 7.28 (d, J=1.6 Hz, 2H), 6.92 (d, J=8.4 Hz, 2H), 3.96 (q, J=6.8 Hz, 2H), 1.43 (t, J=6.8 Hz, 3H). $^{13}$C NMR (100 MHz, CDCl$_3$) δ 147.3, 126.3 (t, J=6.1 Hz), 125.6 (t, J=6.1 Hz), 124.4, 123.5 (t, J=25.2 Hz), 119.3 (tq, J=39.6, 284.6 Hz), 115.2, 113.4 (qt, J=38.2, 253.3 Hz), 42.6, 12.8. GCMS: m/z 463 (67%), 434 (100%), 416 (11%), 394 (11%), 365 (29%), 296 (43%). Anal. calcd. for $C_{18}H_{11}F_{10}NS$ C, 46.66; H, 2.39; N, 3.02. Found C, 46.87; H, 2.25; N, 3.06.

1,2,3,4,6,7,8,9-Octafluorophenothiazine was synthesized following a reported procedure with slight modifications in work-up conditions as described in the following sections.[34, 35]

N-ethyl-1,2,3,4,6,7,8,9-Octafluorophenothiazine (OFEPT) was then synthesized by N-ethylation of octafluorophenothiazine following a previously reported procedure.[24]

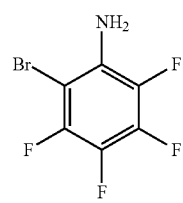

2-Bromo-3,4,5,6-tetrafluoroaniline 2,3,4,5-tetrafluoroaniline (2.50 g, 15.1 mmol) and acetic acid (10 mL) were added under N$_2$ to a 100 mL round-bottomed flask containing a stir bar and fitted with a rubber septum. After dissolution of 2,3,4,5-tetrafluoroaniline, Fe powder (0.085 g, 1.5 mmol) and sodium acetate (1.37 g, 16.7 mmol) were added, and the reaction flask was immersed in an oil bath set at 50° C. A solution of bromine (1.1 mL, 21 mmol) in acetic acid (10 mL) was added dropwise to the reaction mixture, which was stirred for 3 h under $N_2$ before the flask was removed from the oil bath. After the reaction mixture reached rt, the reaction was quenched by adding sodium sulfite (0.20 g, mmol) and aqueous potassium hydroxide (0.20 g in 50 mL water), after which the solution was stirred for 5 min. The product was extracted with dichloromethane, dried over $MgSO_4$, filtered to remove solids, and concentrated by rotary evaporation to obtain the desired product as reddish pink solid (3.20 g, 87%). $^1$H NMR (400 MHz, $CDCl_3$) δ 4.18 (br s, $NH_2$). $^{19}$F NMR (400 MHz, $CDCl_3$) δ −135.9 (m, 1F), −161.0 (m, 1F), −162.6 (m, 1F), −174.0 (m, 1F). $^{13}$C NMR (100 MHz, $CDCl_3$) δ multiple peaks in these ranges: 146.8-130.9, 91.0-91.7. GCMS: m/z 243 (100%), 164 (25%), 137 (46%).

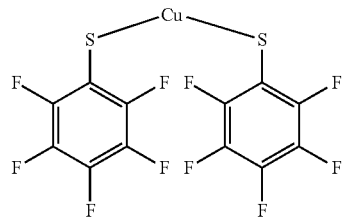

Bis(2,3,4,5,6-pentafluorothiophenolate) copper(II)

Pentafluorothiophenol (2.0 mL, 3.0 g, 15 mmol) was added to a stirred suspension of $Cu_2O$ (1.07 g, 7.50 mmol) in ethanol (22 mL) in a 50 mL round-bottomed flask containing a stir bar and equipped with a reflux condenser. The suspension was immersed in a heated oil bath and was stirred at reflux for 5 h. After removal of the reaction flask from the oil bath and cooling to rt, the reaction mixture was filtered and dried to obtain the product as an off-white solid (4.5 g, 65%). $^{19}$F NMR (400 MHz, $CDCl_3$) δ −134.4 (m, 4F), −150.8 (m, 4F), −162.5 (m, 2F).

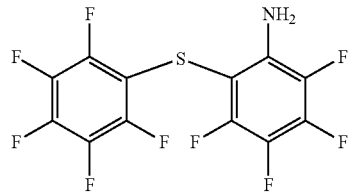 [SMILES: Nc1c(F)c(F)c(F)c(F)c1Sc1c(F)c(F)c(F)c(F)c1F]

2-Amino-nonafluorodiphenyl Sulfide

In an oven-dried 50 mL round-bottomed flask containing a stir bar and fitted with a rubber septum, 2-bromo-3,4,5,6-tetrafluoroaniline (3.00 g, 12.3 mmol), cuprous pentafluorothiophenolate (3.40 g, 7.38 mmol), and anhydrous DMF (12 mL) were combined under $N_2$. The reaction flask was equipped with a reflux condenser and immersed in a heated oil bath. The reaction mixture was stirred at reflux for 2 h under $N_2$. The reaction flask was then removed from the oil bath and allowed to cool to rt, after which the reaction mixture was poured into water. The aqueous mixture was extracted with diethyl ether. The organic layer was dried and concentrated by rotary evaporation to obtain the product as a dark violet solid (3.80 g, 85%). $^1$H NMR (400 MHz, $CDCl_3$) δ 4.61 (br s, $NH_2$). $^{19}$F NMR (400 MHz, $CDCl_3$) δ −134.2 (m, 1F), −135.1 (m, 2F), −153.6 (m, 1F), −155.8 (m, 1F), −163.0 (m, 3F), −174.5 (m, 1F). $^{13}$C NMR (100 MHz, $CDCl_3$) δ multiple peaks in these ranges: 150.3-131.8, 107.1-98.5. GCMS: m/z 363 (100%), 196 (40%).

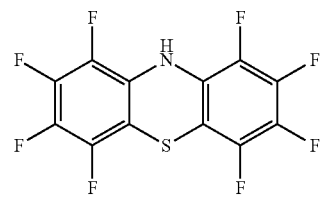 [SMILES: Fc1c(F)c(F)c2c(c1F)Nc1c(F)c(F)c(F)c(F)c1S2]

1,2,3,4,6,7,8,9-Octafluorophenothiazine

In an oven-dried 100 mL round-bottomed flask containing a stir bar, 2-amino-nonafluorodiphenyl sulfide (3.20 g, 8.81 mmol) and 1,4-dioxane (40 mL) were combined, creating a suspension. The flask was fitted with a rubber septum, and sodium hydride (60% dispersion in mineral oil, 0.70 g, 18 mmol) was added under $N_2$. The reaction flask was then equipped with a reflux condenser and immersed in a heated oil bath. The reaction mixture was refluxed for 4 h under $N_2$, after which it was cooled to rt and filtered. The isolated precipitate was dissolved in diethyl ether, and the solution was washed with water, dried over $MgSO_4$, filtered to remove solids, and distilled under vacuum to obtain a grey solid (2.00 g, 67%). The product was crystallized from petroleum ether, obtaining white crystals suitable for analysis by single-crystal X-ray diffraction. $^1$H NMR (400 MHz, $CDCl_3$) δ 6.13 (br s, NH). $^{19}$F NMR (400 MHz, $CDCl_3$) δ −142.0 (m, 1F), −160.0 (m, 1F), −164.0 (m, 1F), −167.2 (m, 1F). $^{13}$C NMR (100 MHz, $CDCl_3$) δ multiple peaks in these ranges: 145.1-135.7, 124.7 (d, J=12.3 Hz), 101.3 (dd, J=3.9, 16.8 Hz). GCMS: m/z 343 (100%), 311 (86%).

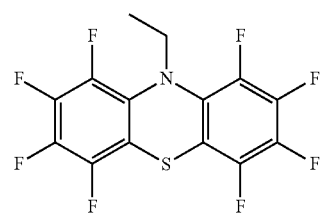 [SMILES: CCN1c2c(F)c(F)c(F)c(F)c2Sc2c(F)c(F)c(F)c(F)c21]

N-Ethyl-1,2,3,4,6,7,8,9-octafluorophenothiazine

An oven-dried 50 mL round-bottomed flask containing a stir bar was fitted with a rubber septum and cooled to rt under $N_2$. Octafluorophenothiazine (0.50 g, 1.5 mmol) and anhydrous DMF (10 mL) were added under $N_2$ to the reaction flask, which was immersed in an oil bath set at 30° C. After 10 min, sodium hydride (60% dispersion in mineral oil, 0.12 g, 3.0 mmol) was added to the reaction mixture. A reflux condenser was attached and the temperature of the oil bath was raised to 50° C. After 20 min at this temperature, bromoethane (0.17 mL, 2.3 mmol) was added dropwise through the condenser. The reaction mixture was stirred under continuous heat and $N_2$ for 6 h. Reaction progress was monitored by GCMS and TLC with hexanes/ethyl acetate (10:1) as the eluent. Upon consumption of the starting material, the reaction flask was removed from the oil bath and allowed to cool to rt, after which the reaction mixture was poured into ice water and the organic product extracted with ethyl acetate. After drying over $MgSO_4$ and treatment with charcoal, the organic layer was filtered to remove solids and was concentrated by rotary evaporation. The crude material was purified via column chromatography with silica gel using hexanes as the eluent, yielding a white solid (0.25 g, 45%). The product was further purified by crystallization from petroleum ether, resulting in white crystals suitable for analysis by single-crystal X-ray diffraction. $^1$H NMR (400 MHz, $CDCl_3$) δ 3.84 (q, J=7.1 Hz, 2H), 1.23 (t, J=7.1 Hz, 3H). $^{19}$F NMR (400 MHz, $CDCl_3$) δ-142.1 (m, 1F), −151.0 (m, 1F), −159.2 (m, 1F), −163.4 (m, 1F). $^{13}$C NMR (100 MHz, $CDCl_3$) δ multiple peaks in these ranges: 144.4-136.9, 129.2 (d, J=10.7 Hz), 113.8 (d, J=18.4 Hz), 50.1 (t, J=5.7 Hz), 14.5. GCMS: m/z 371 (43%), 342 (100%), 310 (29%). Anal. calcd. for $C_{14}H_5F_8NS$ C, 45.29; H, 1.36; N, 3.77. Found C, 45.51; H, 1.30; N, 3.84.

Example 3: Crystal Structures

Figure 9:
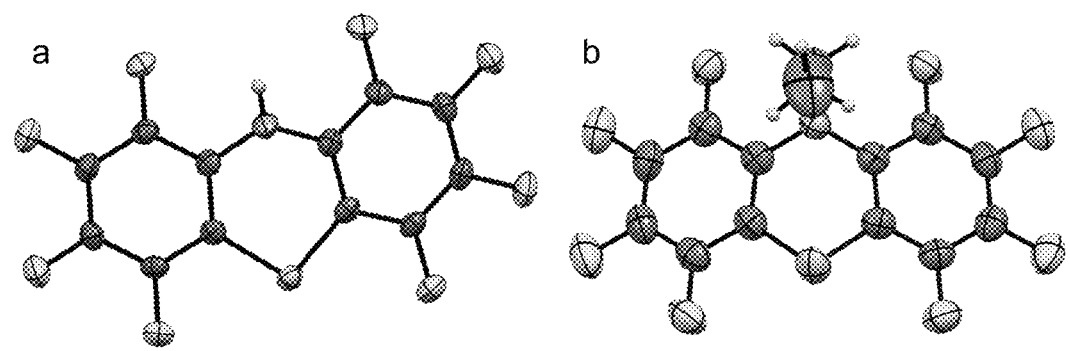
FIG. 9 provides thermal ellipsoid plots for the OFPT (a) and OFEPT (b) obtained by single crystal X-ray diffraction.

X-ray diffraction data was collected at 90K on a Bruker-Nonius X8 Proteum diffractometer. Crystal indexing and data processing were performed with Bruker APEX2 software. With reference to FIG. 9, the structures were solved with shelxt and refined with shelxl-2014.

Example 4: Cyclic Voltammetry

Figure 10:
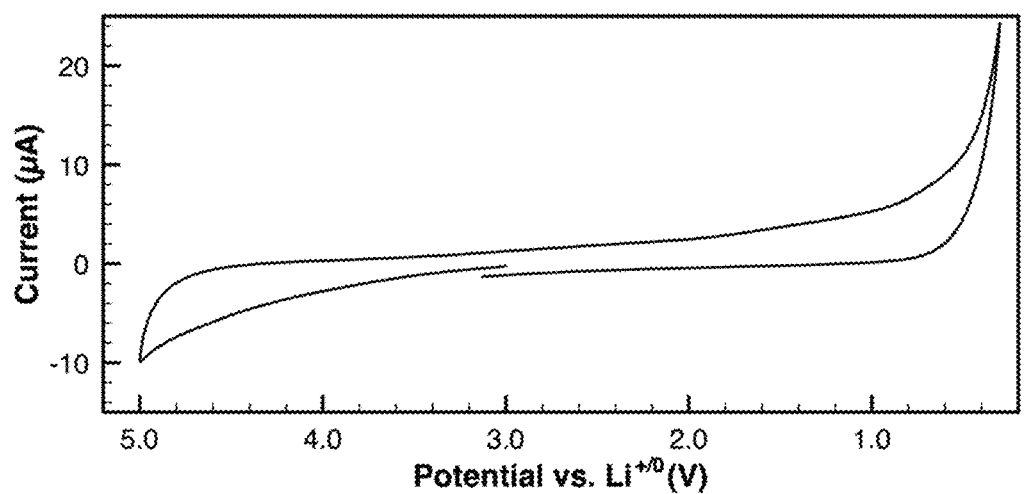
FIG. 10 includes cyclic voltammogram of 1.2 M LiPF$_6$ in EC/EMC (3:7 wt. ratio) recorded at a scan rate of 100 mV/sec.

Cyclic voltammetry (CV) experiments were performed in an argon-filled glovebox using a three-electrode system with a CH Instruments 650E potentiostat. Glassy carbon was used as the working electrode, platinum wire as the counter electrode, and lithium metal as the reference electrode. With reference to FIG. 6 and FIG. 10, voltammograms were recorded in 1.2 M $LiPF_6$ in EC/EMC (3:7 wt. ratio) containing ca. $3.0\times10^{-4}$ M analyte at a scan rate of 100 mV/s.

Example 5: Overcharge Protection

Overcharge tests were conducted by assembling 2032 coin cells in an argon-filled glovebox using $LiFePO_4$ (LFP, Piotrek or MTI) or $LiNi_{0.8}Co_{0.15}Al_{0.05}O_2$(NCA, Argonne National Laboratory's CAMP Facility) as the cathode and synthetic graphite (Gen-2 (MAG-10) or Gen-3 (MCMB), Argonne National Laboratory's CAMP Facility) as the anode (FIG. 7). The electrodes were punched into 14 mm diameter circles and sandwiched around a 15 mm diameter microporous 2325 PP/PE/PP trilayer separator from Celgard. The electrolyte used was 1.2 M $LiPF_6$ in EC/EMC (3:7 wt. ratio), and ca. 85 µL was added to each coin cell. The coin cells were charged with a constant current of C/10 for 20 h or until 5.0 V was reached, followed by a rest of 30 s and discharging to 3.0 V (once again at C/10) using a Landt CT2001A battery cycler.

Example 6: Density Functional Theory Calculations

All density functional theory (DFT) calculations were performed using the Gaussian09 (Revision A.02b) software suite.[38] Geometry optimizations of the neutral and radical-cation states were carried out with the B3LYP functional and 6-311G(d,p) basis set. Frequency analyses for all (fully relaxed) optimized geometries were undertaken to ensure that the geometries were energetic minima.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. P. Arora, R. E. White and M. Doyle, *J. Electrochem. Soc.*, 1998, 145, 3647-3667.
2. P. G. Balakrishnan, R. Ramesh and T. Prem Kumar, *J. Power Sources*, 2006, 155, 401-414.
3. J. Chen, C. Buhrmester and J. R. Dahn, *Electrochem. Solid-State Lett.*, 2005, 8, A59-A62.
4. Z. Chen, Y. Qin and K. Amine, *Electrochim. Acta*, 2009, 54, 5605-5613.
5. C. Buhrmester, L. Moshurchak, R. L. Wang and J. R. Dahn, *J. Electrochem. Soc.*, 2006, 153, A288-A294.
6. C. Buhrmester, J. Chen, L. Moshurchak, J. Jiang, R. L. Wang and J. R. Dahn, *J. Electrochem. Soc.*, 2005, 152, A2390-A2399.
7. J. R. Dahn, J. Jiang, L. M. Moshurchak, M. D. Fleischauer, C. Buhrmester and L. J. Krause, *J. Electrochem. Soc.*, 2005, 152, A1283-A1289.
8. C. Buhrmester, L. M. Moshurchak, R. L. Wang and J. R. Dahn, *J. Electrochem. Soc.*, 2006, 153, A1800-A1804.
9. L. M. Moshurchak, C. Buhrmester and J. R. Dahn, *J. Electrochem. Soc.*, 2008, 155, A129-A131.
10. A. P. Kaur, S. Ergun, C. F. Elliott and S. A. Odom, *J. Mater. Chem. A*, 2014, 2, 18190-18193.
11. A. P. Kaur, C. F. Elliott, S. Ergun and S. A. Odom, *J. Electrochem. Soc.*, 2015, 163, A1-A7.
12. L. Zhang, Z. Zhang, P. C. Redfern, L. A. Curtiss and K. Amine, *Energy Environ. Sci.*, 2012, 5, 8204-8207.
13. J. C. Forgie, S. El Khakani, D. D. MacNeil and D. Rochefort, *Phys. Chem. Chem. Phys.*, 2013, 15, 7713-7721.
14. S.-L. Khakani, J. C. Forgie, D. D. MacNeil and D. Rochefort, *J. Electrochem. Soc.*, 2015, 162, A1432-A1438.
15. S. Ergun, C. F. Elliott, A. P. Kaur, S. R. Parkin and S. A. Odom, *Chem. Commun.*, 2014, 50, 5339-5341.
16. M. Hu, X. Pang and Z. Zhou, *J. Power Sources*, 2013, 237, 229-242.
17. L. M. Moshurchak, W. M. Lamanna, M. Bulinski, R. L. Wang, R. R. Garsuch, J. Jiang, D. Magnuson, M. Triemert and J. R. Dahn, *J. Electrochem. Soc.*, 2009, 156, A309-A312.
18. W. M. Lamanna, M. J. Bulinski, J. R. Dahn, J. Jiang, L. Moshurchak, P. T. Pham, R. L. Wang, US20090286162 A1: 2009.
19. L. Zhang, Z. Zhang, H. Wu and K. Amine, *Energy Environ. Sci.*, 2011, 4, 2858-2862.
20. J. Huang, N. Azimi, L. Cheng, I. A. Shkrob, Z. Xue, J. Zhang, N. L. Dietz Rago, L. A. Curtiss, K. Amine, Z. Zhang and L. Zhang, *J. Mater. Chem. A*, 2015, 3, 10710-10714.
21. M. D. Casselman, A. P. Kaur, K. A. Narayana, C. F. Elliott, C. Risko and S. A. Odom, *Phys. Chem. Chem. Phys.*, 2015, 17, 6905-6912.
22. K. A. Narayana, M. D. Casselman, C. F. Elliott, S. Ergun, S. R. Parkin, C. Risko and S. A. Odom, *ChemPhysChem*, 2015, 16, 1179-1189.

23. S. Ergun, C. F. Elliott, A. P. Kaur, S. R. Parkin and S. A. Odom, *J. Phys. Chem. C*, 2014, 118, 14824-14832.
24. S. A. Odom, S. Ergun, P. P. Poudel and S. R. Parkin, *Energy Environ. Sci.*, 2014, 7, 760-767.
25. M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, and D. J. Fox, Gaussian, Inc., Wallingford Conn., 2009.
26. F. R. Brushett, J. T. Vaughey and A. N. Jansen, *Adv. Energy Mater.*, 2012, 2, 1390-1396.
27. J. Huang, L. Cheng, R. S. Assary, P. Wang, Z. Xue, A. K. Burrell, L. A. Curtiss and L. Zhang, *Adv. Energy Mater.*, 2015, 5, DOI:10.1002/aenm.201401782.
28. A. P. Kaur, N. E. Holubowitch, S. Ergun, C. F. Elliott and S. A. Odom, *Energy Tech.*, 2015, 3, 476-480.
29. X. Wei, W. Xu, M. Vijayakumar, L. Cosimbescu, T. Liu, V. Sprenkle and W. Wang, *Adv. Mater.*, 2014, 26, 7649-7653.
30. M. J. Lacey, J. T. Frith and J. R. Owen, *Electrochem. Commun.*, 2013, 26, 74-76.
31. N. J. Treat, H. Sprafke, J. W. Kramer, P. G. Clark, B. E. Barton, J. Read de Alaniz, B. P. Fors and C. J. Hawker, *J. Am. Chem. Soc.*, 2014, 136, 16096-16101.
32. X. Pan, M. Lamson, J. Yan and K. Matyjaszewski, *ACS Macro Letters*, 2015, 4, 192-196.
33. O. B. Tomilin, E. P. Konovalova, V. N. Yuzhalkin, L. V. Ryabkina and E. P. Sanaeva, *Chem. Heterocycl. Compd.*, 1996, 32, 365-370.
34. G. G. F. Yakobson, L. S. Kobrina and N. N. Vorozhtsov, Jr., *Zhurnal Obshchei Khimii* 1967, 37, 1289-1293.
35. L. J. B. Belf and D. E. M. Wotton, *Chem. Industry*, 1966, 6, 238-239.
36. G. Sheldrick, *Acta Crystallog. Sect. A*, 2015, 71, 3-8.
37. G. Sheldrick, *Acta Crystallog. Sect. C*, 2015, 71, 3-8.
38. G. W. T. M. J. Frisch, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery Jr., J. E. Peralta, F. Ogliaro, M. J. Bearpark, J. Heyd, E. N. Brothers, K. N. Kudin, V. N. Staroverov, R. Kobayashi, J. Normand, K. Raghavachari, A. P. Rendell, J. C. Burant, S. S. Iyengar, J. Tomasi, M. Cossi, N. Rega, N. J. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski and D. J. Fox, 2009, Gaussian, Inc., Wallingford, Conn., USA.
39. A. D. Becke, *J. Chem. Phys.*, 1993, 98, 5648-5652.
40. C. Lang, W. Yang and R. G. Parr, *Phys. Rev. B*, 1988, 37, 785-789.
41. A. D. McLean and G. S. Chandler, *J. Chem. Phys.*, 1980, 72, 5639-5648.
42. R. Krishnan, J. S. Binkley, R. Seeger and J. A. Pople, *J. Chem. Phys.*, 1980, 72, 650-654.
43. Z. Chen and K. Amine, *Electrochem. Commun.*, 2007, 9, 703-707.
44. A. P. Kaur, M. D. Casselman, C. F. Elliott, S. R. Parkin, C. Risko, and S. A. Odom, J. of Materials Chemistry A, 2016, 4, 5410-5414.
45. U.S. Patent Application Publication No. 2011/0294017
46. U.S. Patent Application Publication No. 2011/0294018
47. U.S. Pat. No. 8,101,302

It will be understood that various details of the presently disclosed subject matter can be changed without departing from the scope of the subject matter disclosed herein. Furthermore, the foregoing description is for the purpose of illustration only, and not for the purpose of limitation.

We claim:

1. A compound according to the formula:

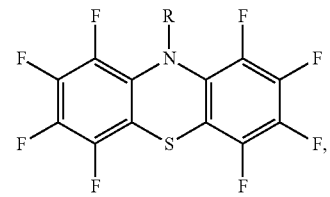

wherein R is selected from the group consisting of alkyl, aryl, alkylaryl, alkoxyaryl, alkylcarboxyl, aryl carbonyl, haloalkyl, perfluoroalkyl, glycols, haloaryl, a negative electrolyte, and a polymer; wherein R is not phenyl.

2. The compound of claim 1, wherein R is alkyl.

3. The compound of claim 2, wherein R is ethyl.

4. A rechargeable battery comprising:
   a high-voltage cathode;
   an electrolyte comprising a charge-carrying medium and a lithium salt;
   a redox shuttle comprising the compound of claim 1.

5. The battery of claim 4, wherein the high-voltage cathode is selected from $LiFePO_4$ (LFP), $LiMn_2O_4$ (LMO), $LiCoO_2$ (LCO), $LiNi_{1/3}Mn_{1/3}Co_{1/3}O_2$ (NMC), and $LiNi_{0.8}Co_{0.15}Al_{0.05}O_2$ (NCA).

6. The battery of claim 4, wherein the compound is provided at a concentration of about 0.05-0.1M.

7. The battery of claim 4, further comprising an electrolyte comprising a charge-carrying medium and a lithium salt.

8. The battery of claim 4 wherein the negative electrode is a graphitic anode.

9. The battery of claim 4, where the compound oxidizes at a potential of about 4.0 V to about 4.8V as compared to Li/Li+.

10. A rechargeable battery comprising:
    a negative electrode;
    a positive electrode; and
    an electrolyte comprising the compound of claim 1.

11. The battery of claim 10 comprising a high-voltage cathode selected from $LiFePO_4$ (LFP), $LiMn_2O_4$ (LMO), $LiCoO_2$ (LCO), $LiNi_{1/3}Mn_{1/3}Co_{1/3}O_2$ (NMC), and LiNi0.8Co0.15Al0.05O2 (NCA).

12. The battery of claim 10, wherein the electrolyte comprises a charge-carrying medium and a lithium salt.

13. The battery of claim 10, wherein the compound is provided in the electrolyte at a concentration of about 0.05-0.1M.

14. The battery of claim 10, wherein the negative electrode is a graphitic anode and the positive electrode is immersed in the electrolyte.

15. A battery comprising a passivating electrolyte additive, wherein the passivating electrolyte additive comprises the compound of claim 1, and wherein the battery is a lithium ion battery or a sodium-ion battery.

16. A battery comprising a photopolymerization initiator or photoredox catalyst, wherein the photopolymerization initiator or photoredox catalyst comprises the compound of claim 1.

17. A battery comprising an electrode material, wherein the electrode material comprises the compound of claim 1.

18. The battery of claim 17, wherein the battery is a non-aqueous redox flow battery.

19. An array comprising two or more of the batteries of claim 4.

20. The array of claim 19, wherein the two or more battery are connected in a series.

\* \* \* \* \*